United States Patent
Gibson et al.

[11] Patent Number: 6,100,391
[45] Date of Patent: Aug. 8, 2000

[54] METHOD FOR MAKING AN ALKYL GLYCOSIDE

[75] Inventors: Michael W. Gibson, Fairfield; Christopher A. Leedy, Cincinnati, both of Ohio

[73] Assignee: Henkel Corporation, Gulph Mills, Pa.

[21] Appl. No.: 09/225,186

[22] Filed: Jan. 4, 1999

Related U.S. Application Data

[60] Provisional application No. 60/070,606, Jan. 6, 1998.

[51] Int. Cl.$^7$ .............................. C07H 1/00; C07H 3/00
[52] U.S. Cl. ..................... 536/124; 536/18.5; 536/18.6
[58] Field of Search ............................. 536/18.5, 18.6, 536/124

[56] References Cited

U.S. PATENT DOCUMENTS

| | | | |
|---|---|---|---|
| 3,450,690 | 6/1969 | Gibbons et al. | 536/124 |
| 4,557,729 | 12/1985 | McDaniel et al. | 8/111 |
| 4,834,903 | 5/1989 | Roth et al. | 252/174.17 |
| 4,939,245 | 7/1990 | Rasche et al. | 536/18.6 |
| 4,950,743 | 8/1990 | McCurry, Jr. et al. | 536/18.6 |
| 4,987,225 | 1/1991 | Pickens et al. | 536/124 |
| 5,003,057 | 3/1991 | McCurry et al. | 536/18.6 |
| 5,206,357 | 4/1993 | Schmidt | 536/18.6 |
| 5,304,639 | 4/1994 | Gibson | 536/18.6 |
| 5,374,716 | 12/1994 | Biermann et al. | 536/18.6 |
| 5,430,141 | 7/1995 | McCurry, Jr. et al. | 536/18.5 |
| 5,457,190 | 10/1995 | Gibson et al. | 536/18.6 |
| 5,496,932 | 3/1996 | McCurry, Jr. et al. | 536/18.5 |
| 5,512,666 | 4/1996 | McCurry, Jr. et al. | 536/18.6 |
| 5,516,747 | 5/1996 | Lachut | 504/116 |
| 5,519,124 | 5/1996 | McCurry, Jr. et al. | 536/18.5 |
| 5,525,256 | 6/1996 | Morris et al. | 252/108 |
| 5,534,500 | 7/1996 | Casamassina et al. | 252/353 |
| 5,545,622 | 8/1996 | Casamassina et al. | 252/353 |
| 5,556,950 | 9/1996 | McCurry, Jr. et al. | 536/4.1 |
| 5,605,683 | 2/1997 | Desai et al. | 424/70.11 |
| 5,633,359 | 5/1997 | Beaulieu | 536/18.6 |
| 5,677,436 | 10/1997 | Desai et al. | 536/4.1 |
| 5,681,938 | 10/1997 | Boiteux et al. | 536/18.6 |
| 5,783,553 | 7/1998 | Desai et al. | 510/470 |

FOREIGN PATENT DOCUMENTS

| | | |
|---|---|---|
| 0387913 | 9/1990 | European Pat. Off. . |
| 0388857 | 9/1990 | European Pat. Off. . |
| 0569682 | 11/1993 | European Pat. Off. . |
| 0700925 | 3/1996 | European Pat. Off. . |

OTHER PUBLICATIONS

Fessenden et al., *Organic Chemistry,* Third Edition, Brooks/Cole Publishing Co., Belmont, California, 1986, only pp. 854–855 supplied. This references kindly supplied by applicant.

*Primary Examiner*—Gary Geist
*Assistant Examiner*—L. Eric Crane
*Attorney, Agent, or Firm*—John E. Drach

[57] ABSTRACT

A process for preparing alkyl polyglycosides by reacting a fatty alcohol with a saccharide in a glycosidation reaction under acidic condition wherein a water-containing emulsion is drawn off from the reaction includes an improvement wherein the emulsion is demulsified by raising the pH of the water-containing emulsion, preferably to a level above 7, whereupon the demulsified water-containing emulsion is allowed to settle into at least a predominantly fatty alcohol containing first layer and a predominantly water-containing second layer. The fatty alcohol-containing layer can be recycled back to the glycosidation reaction. The pH of the water-containing emulsion can be raised by the addition thereto of caustic, such as sodium hydroxide.

30 Claims, 1 Drawing Sheet

METHOD FOR MAKING AN ALKYL GLYCOSIDE

CROSS REFERENCE TO RELATED APPLICATIONS

This application claims priority to U.S. Provisional Application Ser. No. 60/070,606 filed Jan. 6, 1998.

BACKGROUND OF THE INVENTION

The present invention relates to a method for the preparation of alkyl polyglycosides by the reaction of a saccharide and an alcohol, and in particular to a method for treating water emulsion drawn off from the alkyl polyglycoside reaction.

Alkyl glycosides are conveniently prepared by reacting an alcohol of the type and chain length which is desired to form the "alkyl" portion of the glycoside of interest with a saccharide reactant (e.g., a monosaccharide such as glycose, xylose, arabinose, galactose, fructose, etc., or a polysaccharide such as starch, hemicellulose, lactose, maltose, melibiose, etc.) or with a glycoside starting material wherein the aglycone portion thereof is different from the alkyl substituent desired for the ultimate alkyl glycoside product of interest. Typically, such reaction is conducted at an elevated temperature and in the presence of an acid catalyst.

Water is formed as a by-product of the reaction between a fatty alcohol and a saccharide. The water is only sparingly soluble in the fatty alcohol, and undissolved water can result in the formation of unwanted by-products. Consequently, the water is removed as it is formed, usually as part of an emulsion containing fatty alcohol, dextrose, alkyl polyglycosides and organic acids, and is typically collected in a separator. It is desirable to break down this emulsion so that the fatty alcohol can be recovered and recycled. The water, with reduced organic loading, can be disposed of. However, the emulsion cannot easily be broken simply by the use of high temperature (e.g. 150° F.–175° F.) and/or longer residence times. What is needed is a method for breaking down the emulsion quickly and efficiently to facilitate separation of its components.

SUMMARY

A process is provided for preparing alkyl polyglycosides by reacting at least one fatty alcohol with a saccharide source in a glycosidation reaction zone in the presence of an acid; drawing off from the glycosidation reaction zone a mixture including water and a portion of the fatty alcohol, the mixture forming a water-containing emulsion in a liquid state; and adjusting the pH of the water-containing emulsion to a level sufficient to demulsify the water-containing emulsion and to provide at least a predominantly fatty alcohol-containing first layer and a predominantly water-containing second layer.

The process described herein rapidly demulsifies the water-containing emulsion and allows a greater amount of fatty alcohol to be recycled while reducing the organic loading of the water intended for disposal.

DETAILED DESCRIPTION OF PREFERRED EMBODIMENTS

Figure 1:
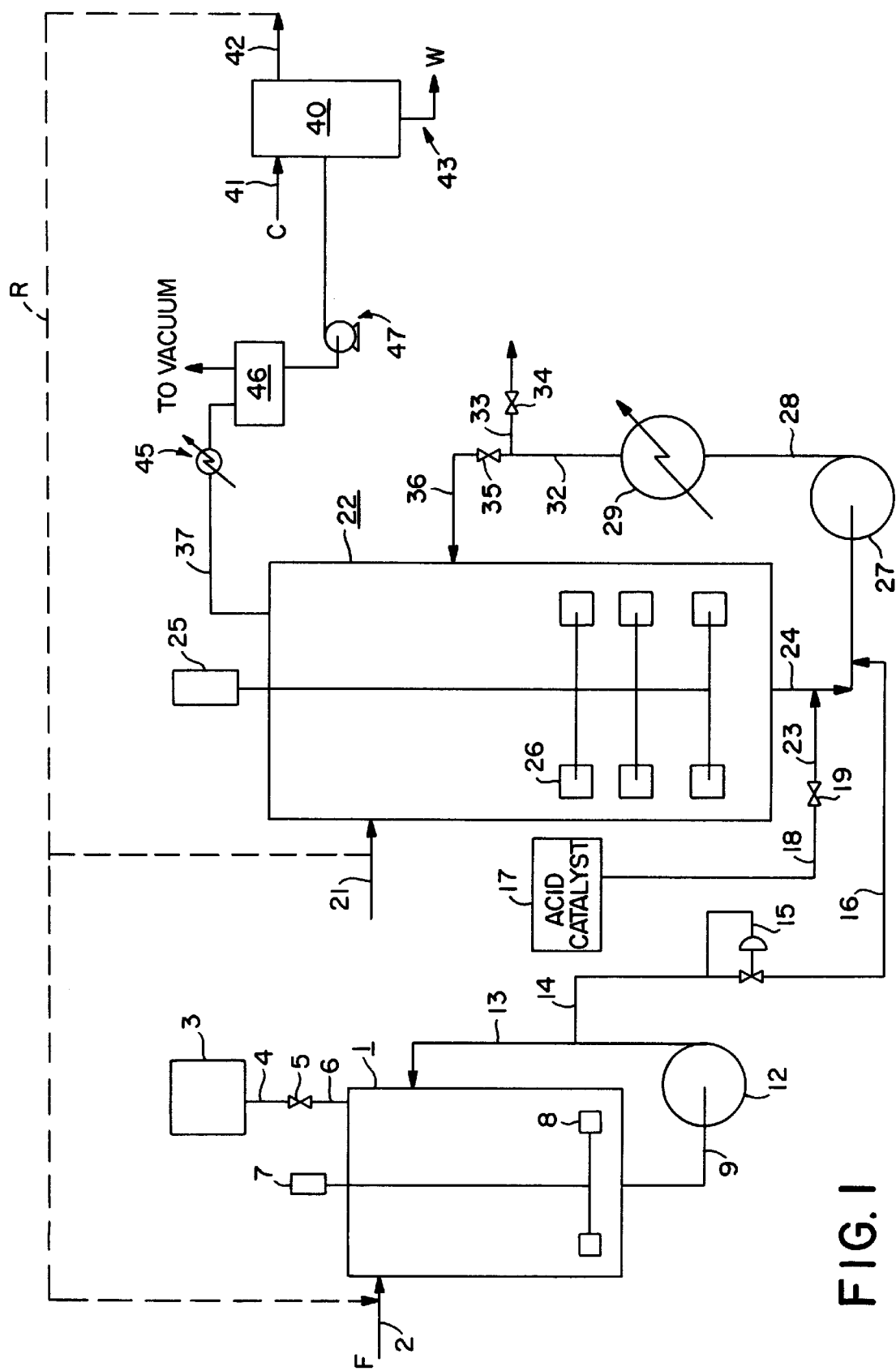
FIG. 1 is a diagrammatic representation of the process of the present invention used in conjunction with a process for preparing alkyl polyglycosides.

Other than in the operating examples, or where otherwise indicated, all numbers expressing quantities, or reaction conditions used herein are to be understood as modified in all instances by the term "about". Composition percentages are by weight unless otherwise indicated.

An "emulsion" as understood herein is a stable mixture of at least two immiscible liquids, wherein one liquid, i.e. the "disperse phase," is suspended in the form of droplets in another liquid, i.e. the "continuous phase". Demulsification is the process of "breaking down" the emulsion to form separate phases, usually as discrete layers of immiscible liquids.

The present disclosure relates to a glycosidation process for preparing alkyl polyglycosides having a long chain alkyl group of 10 or more carbon atoms, by reacting a saccharide with an alcohol having 10 or more carbon atoms in the presence of an acid catalyst at elevated temperatures, after which the acid catalyst is neutralized and the excess alcohol removed.

As disclosed in U.S. Pat. No. 5,457,190, which is herein incorporated by reference in its entirety, a slurry of hydrous saccharide in a first portion of fatty aliphatic alcohol can optionally be introduced into a second portion of the fatty alcohol maintained at an elevated temperature and reduced pressure to form a mixture of saccharide and alcohol with reduced water content. Acid catalyst is introduced into the mixture with reduced water content and the fatty alcohol and saccharide are reacted to form an alkyl glycoside.

As described in the related art section above, the initial reaction product of the alcohol and saccharide in the presence of an acid catalyst results in a glycoside product. The product is a mixture of a monoglycoside of the alcohol and various higher degrees of polymerization (DP) polyglycosides in progressively decreasing mole percentage amounts, i.e., the diglycoside (DP2), the triglycoside (DP3) and the higher polyglycosides (DP4 and higher). The typical, statistical distribution of the various oligomers provided is referred to as a Flory distribution. While the specific distribution of the various fractions may vary somewhat for various reaction products, the overall distribution curve is the same, though the average DP of the reaction mixture may vary due to the differing distribution of the various fractions, i.e., DP1, DP2, DP3 and higher fractions. Typically, the Flory distribution of the reaction product after removal of the excess alcohol will have an average degree of polymerization above 1.2, i.e., about 1.4, with a monoglycoside content in the range of about 50–70% by weight of the glycoside product. Commercially available products typically have an average Flory DP of about 1.3–1.7.

The glycoside products of the reaction of an alcohol and saccharide may be represented by formula I:

$$ROG_x \hspace{4cm} (I)$$

wherein R is a residue of an alcohol, O is oxygen, G is a glycoside residue, and x is the average degree of polymerization (DP) resulting from weighing of the various mono-, di-, tri- and higher glycoside fractions present in the product and is a number of from about one to about three.

The average degree of polymerization is thus defined as the ratio of saccharide rings to the R groups in the alkyl glycoside. The monoglycoside fraction would have one saccharide ring, the diglycoside would have 2, the triglycoside would have 3 with the higher glycoside having corresponding more rings, the average of which in the currently available commercial product therefore being typically greater than about 1, generally in the order of about 1.2 to about 1.7, with preferred mixtures at about 1.3 to about 1.7.

The alkyl polyglycoside products represented by the formula above contain a lipophilic group, the R group, and a hydrophilic group, the $OG_x$ group. For detergent or surfactant use application, the product should have a hydrophilic/lipophilic balance (HLB) of from about 10 to about 16, and preferably about 11 to about 14. The HLB value of a product may be calculated by the formula $$HLB = \frac{([MW_{AGU}] \times DP + MW_o)}{(([MW_{AGU}] \times DP + MW_o) + MW_R)} \times 100/5$$

where AGU is typically the anhydro glycose unit in G having a molecular weight of 162, $MW_o$ is the molecular weight of oxygen and $MW_R$ is the molecular weight of the R group, and DP is the average degree of polymerization as predicted by Flory's statistical treatment.

The lipophilic R groups in the alkyl polyglycosides are derived from alcohols, preferably monohydric, for the detergent, surfactant-use applications and should contain from about 8 to about 20, preferably about 10 to about 18 carbon atoms, with an average of about 10 to about 14 being most preferred, to provide R groups of sufficient length for detergent, surfactant-use applications. While the preferred R groups are saturated aliphatic or alkyl, there may be present some unsaturated aliphatic hydrocarbon groups. Thus, the preferred groups are derived from the fatty alcohols derived from the naturally-occurring fats and oils, such as octyl, decyl, dodecyl, tetradecyl, hexadecyl, octadecyl, oleyl and linoleyl, but R groups may be derived from synthetically produced Ziegler alcohols or oxo alcohols containing 9, 10, 11, 12, 13, 14 or 15 carbon atoms. The alcohols of naturally-occurring fatty acids typically contain an even number of carbon atoms and mixtures of alcohols are commercially available such as mixtures of $C_8$ and $C_{10}$, $C_{12}$ and $C_{14}$, and the like. Synthetically-produced alcohols, for example those produced by an oxo process, contain both an odd and even number of carbon atoms such as the $C_9$–$C_{15}$ mixtures, which are also available commercially.

Saccharide reactants which can be employed to prepare the aforementioned glycoside surfactants include reducing monosaccharide materials containing 5 or 6 carbon atoms such as, for example, glucose, galactose, mannose, xylose, arabinose, fructose, etc. as well as materials which are hydrolyzable to form monosaccharides such as lower alkyl glycosides (e.g. a methyl glycoside, an ethyl glycoside, a propyl glycoside, a butyl glycoside, etc.), oligosaccharides (e.g. sucrose, maltose, maltotriose, lactose, xylobiose, melibiose, cellobiose, raffinose, stachyose, etc.) and other polysaccharides. Glucose is preferred. Such saccharide reactants may be employed in dry (e.g. anhydrous) form or, if desired, may be employed in the form of hydrated solids or aqueous solutions thereof. If utilized in the form of a solution, it is preferred that the resulting reaction mixture contain only small amounts of water, i.e., less than about 1% by weight, preferably less than about 0.5% i.e. less than 0.25% or 0.1%.

The molar ratio of alcohol to monosaccharide in the reaction mixture can vary widely but is typically between about 1.5:1 to about 10:1, and preferably between about 2.0:1 to about 6.0:1. The particular molar ratio chosen depends upon the desired average degree of polymerization (DP) of the monosaccharide reacted with the alcohol. Preferably, the ratio of alcohol to monosaccharide will be chosen to allow the production of an alkyl glycoside product having a DP between about 1.2 to about 1.7, and more preferably about 1.3 and about 1.6.

The reaction between the hydrophobic alcohol reactant and the saccharide reactant to form the glycoside surfactant is typically conducted at an elevated temperature and in the presence of an acid catalyst. As a general rule, the reaction is preferably conducted at a temperature of from about 80° C. to about 140° C., preferably 90° C. to about 120° C., and at pressures (about 10 to about 100 mm Hg absolute), which facilitate water removal, while at the same time maintaining the desired reaction temperatures.

Acid catalysts suitable for use include strong mineral acids such as hydrochloric acid, sulfuric acid, nitric acid, phosphoric acid, hypophosphorous acid, etc.; strong organic acids such as para-toluenesulfonic acid, methanesulfonic acid, trifluoromethanesulfonic acid, mono- or polyalkylated aryl mono- or polysulfonic acids such as dodecylbenzene sulfonic acid, alpha-sulfocarboxylic acids or esters, etc.; and macroreticular acidic ion exchange resins such as macroreticular sulfonic acid ion exchange resins, perfluorinated sulfonic acid resins, etc. Typically, said acid catalyst will be employed in an amount ranging from about 0.0005 to about 0.03 (preferably from about 0.002 to about 0.015) moles thereof per mole of saccharide used.

As indicated above, it is desirable to remove water from the reaction as soon as it is formed. Water is generally removed by distillation under the aforementioned reaction conditions of elevated temperature and reduced pressure. However, the water is withdrawn in the form of a mixture containing fatty alcohol, dextrose, alkyl polyglycosides, and organic acids, which form an emulsion when condensed to a liquid state, and is typically collected in a separator. It is desirable to break down the emulsion quickly and efficiently to recycle the organics and reduce the organic loading of the water which can then be sent to disposal facilities. Surprisingly, it has been found that by increasing the pH of the water emulsion to a level above 7 the emulsion can be rapidly demulsified.

Referring now to FIG. 1 an exemplary method of the present invention is illustrated in conjunction with the process for preparing alkyl polyglycosides. Vessel 1 is a vessel for preparing a slurry of a hydrous saccharide source in a fatty alcohol. A predetermined amount of fatty alcohol feed F is introduced into vessel 1 through line 2. The fatty alcohol feed F can contain virgin fatty alcohol optionally with recycled fatty alcohol, as explained below. The fatty alcohol is generally at a temperature in the range of from about 20° C. to about 50° C. The agitation means 7 having rotating impeller 8 is placed in motion after the required amount of fatty alcohol has been introduced into vessel 1.

The fatty alcohol in vessel 1 is circulated in the vessel through line 9, pump 12 and line 13. Vessel 3 is a hydrous saccharide source storage zone. A predetermined amount of the hydrous saccharide source is introduced into storage zone 3. After the alcohol has been introduced into vessel 1 and the mixing means 7 and circulating pump 12 have been placed in operation, the hydrous saccharide source is introduced into vessel 1 through line 4, valve means 5 which can be a star feeder valve or its equivalent and line 6 into the fatty alcohol in vessel 1.

Mixing means 7 can be a high shear mixer, an agitator or other means which provides a suspension of finely divided hydrous saccharide source in a first portion of fatty alcohol. Vessel 1 can have heating and cooling means or have a heat exchange means in line 13 between pump 12 and vessel 1. Heat exchange means in line 13 or associated with vessel 1 are not shown. However, it would be well known to one skilled in the art that a jacket or coils could be welded to the external surfaces of vessel 1 or a shell and tube heat exchanger included in line 13 to provide heating or cooling to the slurry of the hydrous saccharide source in the first portion of fatty alcohol. The slurry of the hydrous saccharide source in the first portion of fatty alcohol is agitated by mixing means 7 and circulated by means of circulating pump means 12 to maintain the solid hydrous saccharide source suspended in the first portion of fatty alcohol.

A second portion of fatty alcohol is introduced via line 21 into dehydration and glycosidation reaction vessel 22. The second portion of the fatty alcohol can be hot fatty alcohol which has been recovered from a previous reaction sequence or virgin alcohol which has been heated to an elevated temperature, recycled fatty alcohol, or a combination thereof. The second portion of the fatty alcohol can be heated by circulation of the fatty alcohol through line 24, pump means 27, line 28, heat exchanger 29, line 32, valve 35 and line 36. The dehydration and reaction vessel 22 can also have a heating jacket or heating coils affixed to the sides and bottom of the vessel (not shown). When the second portion of the fatty alcohol has been introduced into vessel 22, the mixing means 25 is activated and mixing elements 26 rotated in the vessel. The mixing means 25 and pumping means are useful to prevent the finely divided hydrous or anhydrous saccharide particles from settling in the vessel and to permit rapid removal of water from the mixture.

After the second portion of the fatty alcohol has been heated to the required temperature and the pressure in vessel 22 has been reduced to the required pressure through line 37 to the vacuum system (not shown), a controlled stream of the slurry of hydrous source of saccharide is introduced into dehydration and reaction vessel 22 through line 14, flow control means 15, and line 16. The slurry of the hydrous saccharide source in the first portion of fatty alcohol is introduced into suction line 24 of pump 27 and is circulated through heat exchanger 29 to dehydration and reaction vessel 22.

The temperature in the reaction vessel is maintained at the desired level (generally below about 110° C.) by controlling the heat introduced into the second portion of the fatty alcohol by heat exchanger 29 or any other heating means in the system and the rate at which the slurry of the hydrous saccharide source in the first portion of the fatty alcohol is introduced into vessel 22. The temperature of the mixture is maintained at a temperature sufficiently high to remove at least a portion of the water associated with the hydrous saccharide source but below a temperature at which the hydrous saccharide source melts or forms a syrup before water is removed. As water is removed the temperature can be ramped when the saccharide source tends to liquify at elevated temperature.

After all of the slurry of the hydrous saccharide source in the first portion of the fatty alcohol has been introduced into dehydration and reaction vessel 22, the temperature of the mixture of the first portion and the second portion of the fatty alcohol and the saccharide source is maintained at or rapidly raised to the temperature at which catalyst is to be added. The pressure in the vessel is maintained at a low level and any remaining water associated with the hydrous saccharide source is removed. The reduced pressure which can be maintained in dehydration and reaction vessel 22 is dependent upon the fatty alcohol to be reacted and the capabilities of the vacuum producing system. Since the reaction is to be carried out at a temperature in the range of from about 90° C. to about 140° C., preferably 95° C. to 130° C., the reduced pressure which can be maintained on a $C_7$ alcohol is higher than one which can be maintained when a $C_{22}$ fatty alcohol is utilized as the reactant. The pressure must be as low as possible without boiling a substantial amount of the fatty alcohol from the reaction mixture.

After the amount of water in the mixture has been reduced to the required level, an acid catalyst in vessel 17 is introduced into the mixture of saccharide and fatty alcohol through line 18, valve means 19 and line 23 into the suction line 24 of pump 27. The acid catalyst is introduced into the circulating slurry of saccharide source in fatty alcohol at a rate such that the concentration of the acid catalyst in the fatty alcohol slurry in the catalyst addition zone remains low.

If the mixture of fatty alcohol and saccharide source is at the required temperature, as soon as the acid catalyst is introduced into the mixture, the fatty alcohol begins reacting with the saccharide source to form the aliphatic glycoside. With aqueous solutions of polar catalysts a temperature lower than reaction temperature is selected for catalyst addition. After catalyst addition, the temperature is raised to promote the desired reaction rate.

The mixture of the saccharide source and the fatty alcohol is reacted for from about 1 to about 15 hours after the acid catalyst has been introduced into the mixture. The reaction is carried out until the amount of unreacted saccharide source in the mixture has reached a predetermined level. Generally, the amount of unreacted saccharide source in the reaction mixture is less than about 5% by weight of the alkyl glycoside formed and preferably less than about 2% by weight of the glycoside formed and most preferably less than 0.25% by weight of the aliphatic glycoside formed.

After the reaction has been substantially completed, the reaction mixture can be cooled by circulating the reaction mixture through line 24, circulating pump 27, line 28, heat exchange means 29 which now becomes a reaction product cooling means, line 32, valve 35 and line 36.

After the reaction mixture has been cooled to a predetermined temperature, the reaction mixture can be removed from vessel 22 by closing valve 35 in line 32 and opening valve 34 in line 33 and pumping the mixture to the product recovery portion of the process for further treatment.

In an alternative method, after the reaction mixture has been reduced to the required residual saccharide content, a neutralizing material such as an alkali metal hydroxide, alkali earth metal oxide or alkali earth metal hydroxide can be added to vessel 22 to neutralize the acid catalyst. As is well known in the art, the neutralized mixture is then passed to a means for separating the unreacted fatty alcohol to recover the aliphatic glycoside and the aliphatic glycoside can be mixed with water and/or further treated to reduce the color, stabilize the color and dilute the material to the concentration at which it is to be sold. Generally, the aliphatic glycosides are sold as aqueous mixtures containing from about 30% to about 80% by weight of the active surfactant material.

As mentioned above, the reaction of the saccharide source with the fatty alcohol produces water. The water is removed from the reacting mixture as soon as it is formed due to the elevated temperature and the reduced pressure maintained on the reacting mixture. The water is removed as a vapor, which is condensed to form a water-containing emulsion, which typically contains fatty alcohol, organic acids, and other organic components as well as water.

The components of the water-containing emulsion are continuously removed as a vapor via line 37, which is under vacuum. These components are condensed by heat exchanger 45 into a liquid water-containing emulsion which is then sent to a collector 46. The liquid is drawn off by pump 47 and is sent to separator 40, which is at atmospheric or above atmospheric pressure. The water-containing emulsion obtained from vessel 22 typically has a pH of about 2 to 3 because of organic acids formed as reaction by products present in the emulsion. Caustic C is added to the separator via line 41, or alternatively to line 37 prior to the entry of the water-containing emulsion into the separator, to increase the pH of the emulsion to a level of from above 7, preferably from 8 to 13, and more preferably 9 to 12. Treatment with caustic causes rapid demulsification of the water-containing emulsion, which can then be allowed to settle into at least top and bottom layers, as described below. Preferably the caustic is a aqueous solution of a base such as sodium hydroxide ranging from 5% to 50% NaOH, more preferably from 10% to 40% NaOH, and most preferably from 20% to 30% NaOH. Other percentages can also be used when deemed appropriate. Also, the sodium hydroxide can be added in solid form. The amount of caustic added is such as to raise the pH to above 7, preferably 8 to 13, and more preferably 9 to 12. For a 25% solution of NaOH the caustic would be about 2 to 3% by weight of the amount of water emulsion. Other bases can be used in place of or in addition to NaOH, such as potassium hydroxide KOH, aluminum hydroxide $Al(OH)_3$, calcium hydroxide $Ca(OH)_2$, alkyl amines, ammonia, and the like, either in aqueous solution, neat liquids, or solids.

The separator 40 is preferably maintained at an elevated temperature, e.g. 50° C. to about 100° C. for a separator vessel maintained at atmospheric pressure. At higher pressures the separator can be maintained at a temperature of from about 50° C. to about 200° C., more preferably from about 80° C. to about 175° C. for a period of time ranging from about 1 hour to 4 hours. Preferably the contents of the separator 40 are then allowed to cool, whereupon the contents settle out into layers. The top layer contains mostly fatty alcohol having a moisture content no more than about 5% and can be removed via line 42 and optionally returned to the vessel 1 via recycle stream R to fatty alcohol feed line 2 or feed line 21. The bottom layer is water which can be removed as waste W via line 43. By raising the pH to a pH level of above 7, preferably from 8 to 13 and more preferably from 9 to 12 a 45% reduction of Chemical Oxygen Demand ("COD") can be achieved. COD provides a measure of organic content. Thus, it is desirable that the water for disposal have a low COD value. Using the method of the present invention the COD value of the water removed for disposal can be reduced to a level of no more than about 26,000. With the addition of about 1.5% mass of caustic added to the separator, alcohol recovery can be increased from about 3% (without treatment) to over 30% (with treatment), i.e. more than a 10 fold improvement in alcohol recovery.

The following examples are presented as further exemplifications of the invention herein and not as limitations of its scope.

EXAMPLE 1

Samples were taken from an under flow line of a decanter containing water emulsion drawn off from an alkyl polyglycoside ("APG") production reactor. Sample 1 had no caustic added to it and served as a control. A 25% caustic NaOH solution was added to Sample 2 to 6 sufficient to raise pH of the sample to the indicated level set forth below in Table 1. The samples were then placed in an oven set at 80° C. for a period of 4 hours. After allowing the samples to cool to ambient temperature a COD analysis was performed on each sample. The COD of the water was measured according to the Method 2030 Hack Company and approved by the United States Environmental Protection Agency for reporting purposes. The COD is reported as milligrams/liter. The results are set forth in Table 1.

TABLE 1

| Sample No. | pH | COD value | Caustic Added (g) | Sample Mass (g) | Percent Added | Percent Reduction in COD |
|---|---|---|---|---|---|---|
| 1 | 2.5 | 45,000 | None | — | — | — |
| 2 | 7.0 | 21,500 | 2.6 | 205.0 | 1.27% | 52.2% |
| 3 | 8.6 | 21,000 | 2.3 | 205.7 | 1.12% | 53.3% |
| 4 | 10.2 | 22,500 | 2.5 | 216.3 | 1.16% | 50.0% |
| 5 | 11.1 | 26,000 | 2.1 | 199.4 | 1.05% | 42.2% |
| 6 | 12.0 | 23,500 | 5.1 | 205.9 | 2.48% | 47.8% |

As can be seen from Table 1, addition of caustic to the emulsion produced up to 53% reduction in the organic loading of the samples, thereby indicating a separation of the emulsion with reduced organic content in the water.

EXAMPLE 2

Samples were collected from a decanter as in Example 1 except that the samples were drawn off from a higher point in the decanter. The samples were treated in the manner similar to the procedure set forth in Example 1, Sample 7 being the control with no caustic added. The results are set forth below in Table 2.

TABLE 2

| Sample No. | pH | COD value | Caustic Added (g) | Sample Mass (g) | Percent Added | Percent Reduction in COD |
|---|---|---|---|---|---|---|
| 7 | 2.5 | 146,000 | None | — | — | — |
| 8 | 9.5 | 60,500 | 2.8 | 212.8 | 1.32% | 58.6% |
| 9 | 10.1 | 65,500 | 3.3 | 188.7 | 1.75% | 55.1% |
| 10 | 10.6 | 64,000 | 2.8 | 204.6 | 1.37% | 56.2% |
| 11 | 11.1 | 85,500 | 3.0 | 212.0 | 1.42% | 41.4% |
| 12 | 12.1 | 79,500 | 5.4 | 212.9 | 2.54% | 45.5% |

Further lab analysis of the samples in this Example 2 showed great increase in potential alcohol recovery. The control sample No. 7 had only two layers, a top layer ⅛" thick and a bottom emulsion layer which was 3½" thick. The top layer had a 0.9638 specific gravity at 20° C. and a moisture content of 68%. Sample No. 10, which was taken to a pH of 10.6, had three different layers. The top layer was 1⅛" thick, the middle layer ⅛", and the bottom 2¹⁄₁₆". The specific gravity of the top layer was 0.856, while the bottom was 1.018 at 20° C. The moisture content of the top layer was found to be 4.96%. The above results indicate that a return of 34% alcohol is feasible with caustic treatment as opposed to a 3% return without treatment. The quality of the alcohol returned is also higher. Similar returns were found for all treated samples. The only visual difference between the samples was a darker appearance as more caustic was added.

EXAMPLE 3

Water emulsion drawn off from an APG reactor was allowed to settle in a separator tank for two days. At the start of the test sampling for this Example there was a 4.5 inch to 5.5 inch thick layer of fatty alcohol available for recovery at the top of the tank contents. The temperature of the tank at the start of the test was 150° F. Control samples of emulsion were drawn off at different levels in the tank: level A (top), level B (intermediate), level C (intermediate and below level B), and level D (bottom underflow). The pH of the control samples was about 2.5. The samples were tested for COD value in accordance with the method stated above. The results are set forth below in Table 3.

TABLE 3

| Sample No. | Tank Level | COD of Untreated Control |
|---|---|---|
| 13 | A | 177,000 |
| 14 | B | 143,000 |
| 15 | C | 167,000 |
| 16 | D | 87,000 |

Next about 2000 lbs of caustic solution (25% aqueous NaOH) was added and the tank contents were agitated for better mixing by recirculation for one hour. During recirculation the tank heated to a temperature of 175° F. The tank contents were then allowed to settle for 30 minutes into different layers. The top layer was a 30 inch thick layer of alcohol having a 4.9% water content available for recovery. Samples were taken from the different levels of the tank. The results are set forth below in Table 4.

TABLE 4

| Sample No. | Tank Level | pH | COD Value | % COD Reduction Compared to Control |
|---|---|---|---|---|
| 17 | A | 8.23 | Alcohol | — |
| 18 | B | 8.77 | 45,500 | 68.2% |
| 19 | C | 9.32 | 46,000 | 72.5% |
| 20 | D | 13.43 | 21,500 | 75.3% |

The following day samples were collected again to see if further change occurred overnight. The samples were collected at the indicated levels and the COD values were compared with those of the control samples (Table 3) to determine percentage COD reduction. The results are set forth below in Table 5.

TABLE 5

| Sample No. | Tank Level | pH | COD Value | % COD Reduction Compared to Control |
|---|---|---|---|---|
| 21 | A | 7.15 | Alcohol | — |
| 22 | B | 7.26 | 47,500 | 66.8% |
| 23 | C | 10.28 | 43,000 | 74.3% |
| 24 | D | 13.23 | 22,000 | 74.73% |

The moisture content of the alcohol sample No. 21 was determined to be 3.2%.

As can be seen from the above, alcohol recovery increased from a 4.5"–5.5" thick layer before treatment, to 30" thick layer after treatment, representing about a 6-fold improvement.

Water leaving the separator had about a 70% lower COD level. The breakup of the emulsion is very rapid, i.e. upon addition and mixing of the caustic, and further waiting is not necessary.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for preparing alkyl polyglycosides comprising:
   (a) reacting at least one fatty alcohol with a saccharide source in a glycosidation reaction zone in the presence of an acid;
   (b) transferring from the glycosidation reaction zone to a second zone a mixture including water and a portion of the fatty alcohol, the mixture forming a water-containing emulsion in a liquid state; and
   (c) adjusting the pH of the water-containing emulsion in the second zone by raising the pH to a level above 7 to demulsify the water-containing emulsion and to provide at least a predominantly fatty alcohol-containing first layer and a predominantly water-containing second layer.

2. The process of claim 1 further comprising adding an alkaline material to the glycosidation reaction zone.

3. The process of claim 1 wherein the pH of the water-containing emulsion is raised to a level of from about 8 to about 13.

4. The process of claim 1 wherein the pH of the water-containing emulsion is raised to a level of from about 9 to about 12.

5. The process of claim 1 wherein adjusting the pH of the water-containing emulsion comprises adding an alkaline material to the water-containing emulsion.

6. The process of claim 5 wherein the alkaline material is selected from the group consisting of sodium hydroxide, potassium hydroxide, aluminum hydroxide, calcium hydroxide, alkylamine and ammonia.

7. The process of claim 5 wherein the alkaline material comprises an aqueous solution of sodium hydroxide.

8. The process of claim 7 wherein the aqueous solution of sodium hydroxide has a concentration of from about 5% to about 50% by weight of sodium hydroxide.

9. The process of claim 5 wherein adjusting the pH of the water-containing emulsion further comprises maintaining the water-containing emulsion at a temperature of from about 80° C. to about 175° C. for from about 1 hour to 4 hours while mixing the caustic and water-containing emulsion.

10. The process of claim 1 further comprising the step of recycling the predominantly fatty alcohol-containing first layer to the glycosidation reaction zone.

11. The process of claim 1 wherein the predominantly fatty alcohol-containing first layer has a moisture content no more than about 5% by weight.

12. The process of claim 1 wherein the predominantly water-containing layer has a Chemical Oxygen Demand of no more than about 26,000.

13. The process of claim 1 wherein the fatty alcohol has an aliphatic moiety containing from about 8 to 20 carbon atoms.

14. The process of claim 1 wherein the fatty alcohol has an aliphatic moiety containing from about 10 to 18 carbon atoms.

15. The process of claim 1 wherein the fatty alcohol has an aliphatic moiety containing from about 10 to 14 carbon atoms.

16. The process of claim 1 wherein the saccharide source is selected from the group consisting of glucose, galactose, mannose, xylose, arabinose, fructose, sucrose, maltose, maltotriose, lactose, xylobiose, melibiose, cellobiose, raffinose, a methyl glycoside an ethyl glycoside, a propyl glycoside and a butyl glycoside.

17. The process of claim 1 wherein the saccharide is glucose.

18. The process of claim 1 wherein the acid is selected from the group consisting of hydrochloric acid, sulfuric acid, nitric acid, phosphoric acid, hypophosphorous acid, para-toluene sulfonic acid, dodecylbenzene sulfonic acid, alpha-sulfocarboxylic acid, macroreticular sulfonic acid ion-exchange resin and perfluorinated sulfonic acid resin.

19. The process of claim 1 wherein the glycosidation reaction is carried out at a temperature ranging from about 80° C. to about 140° C.

20. The process of claim 2 wherein the alkaline material is selected from the group consisting of alkali metal hydroxide, alkaline earth metal hydroxide and alkaline earth metal oxide.

21. A process for preparing alkyl polyglycosides comprising:
   a) reacting a fatty alcohol compound having an aliphatic moiety containing from about 8 to 20 carbon atoms with a saccharide source in a glycosidation reaction zone in the presence of an acid, wherein the saccharide source is selected from the group consisting of glucose, galactose, mannose, xylose, arabinose, fructose, sucrose, maltose, maltotriose, lactose, xylobiose, melibiose, cellobiose, raffinose, a methyl glycoside, an ethyl glycoside, a propyl glycoside and a butyl glycoside;
   b) transferring from the glycosidation reaction zone to a second zone a mixture including water and a portion of the fatty alcohol, which form a water-containing emulsion; and
   c) adjusting the pH of the water-containing emulsion in the second zone by raising the pH to a level above 7 to demulsify the water-containing emulsion and to provide at least a predominantly fatty alcohol-containing first layer and a predominantly water-containing second layer.

22. The process of claim 21 further including the step of recycling the fatty alcohol-containing first layer back to the glycosidation reaction zone.

23. The process of claim 21 wherein the saccharide source is glucose.

24. The process of claim 21 wherein the molar ratio of alcohol to saccharide source is chosen to produce an alkyl polyglycoside product having a Flory degree of polymerization of from about 1.2 to about 1.7.

25. The process of claim 21 wherein the molar ratio of alcohol to saccharide source is between about 1.5:1 and about 10:1.

26. The process of claim 21 wherein the molar ratio of alcohol to saccharide source is between about 2.0:1 and about 6.0:1.

27. The process of claim 21 wherein the pH is raised to a level of from about 8 to about 13.

28. The process of claim 21 wherein the pH is raised to a level of from about 9 to about 12.

29. The process of claim 21 wherein in the step of adjusting the pH of the water-containing emulsion caustic is added to the water-containing emulsion.

30. The process of claim 22 wherein the caustic comprises a solution of sodium hydroxide.

* * * * *